United States Patent [19]

Jones

[11] Patent Number: 5,147,880
[45] Date of Patent: Sep. 15, 1992

[54] BENZO[A]FLUORENE COMPOUNDS

[75] Inventor: Charles D. Jones, Indianapolis, Ind.

[73] Assignee: Eli Lilly and Company, Indianapolis, Ind.

[21] Appl. No.: 733,529

[22] Filed: Jul. 22, 1991

[51] Int. Cl.$^5$ ............... A61K 31/445; C07C 211/31; C07D 211/00

[52] U.S. Cl. ................... 514/319; 514/212; 514/428; 514/650; 540/609; 546/195; 548/528; 564/337; 564/347; 564/353; 564/354

[58] Field of Search ............ 548/528; 546/195; 540/609; 564/337, 347, 353, 354; 514/212, 319, 428, 650

[56] References Cited

U.S. PATENT DOCUMENTS

| | | | |
|---|---|---|---|
| 4,230,862 | 10/1980 | Suarez | 546/237 |
| 4,418,068 | 11/1983 | Jones | 546/202 |
| 4,677,193 | 6/1987 | Rivier | 530/313 |

OTHER PUBLICATIONS

Fujisaki et al "Restriction Rotation around . . . " Nippon Kasaku Kaishi 739-742 (1979).
Gomberg and Blicke "Triphenylmethyl . . . " JACS 45 1765-1779 (1923).
Gomberg and Blicke "Halochromic Salts . . . " JACS 57 119-124 (1935).
Lansbury et al "Intramolecular 1,3-Proton Transfer . . . " JACS 90 6544-6546 (1968).

Primary Examiner—C. Warren Ivy
Assistant Examiner—Celia Chang
Attorney, Agent, or Firm—Joseph A. Jones; Leroy Whitaker

[57] ABSTRACT

Benzo[a]fluorenes having an aminoalkoxy group on a phenyl ring at the 11-position have estrogenic and antiestrogenic activity.

18 Claims, No Drawings

BENZO[A]FLUORENE COMPOUNDS

FIELD OF THE INVENTION

This invention belongs to the fields of pharmaceutical and synthetic organic chemistry. It provides new benzo [a] fluorenes which have pharmaceutical activities.

BACKGROUND OF THE INVENTION

The benzofluorenes have been explored in the organic chemical literature to some extent. Lansbury and Fountain showed 11-phenyl-11H-benzo[a]fluorene in *J. Am. Chem. Soc.* 90, 6544 (1968). Dilthey showed 11-(4-bromophenyl)-11H-benzo[a]fluorene, *J. Prakt. Chem.* 2, 109, 319 (1925). However, it appears that benzofluorenes have not been extensively explored by pharmaceutical chemists.

For some years, however, compounds with anti-estrogenic and estrogenic activity have been studied. A number of such compounds have been shown to have useful anti-neoplastic activity; see, for example, Jones, U.S. Pat. No. 4,418,068, which shows a series of benzo[b]thiophenes.

More recently, the medical and pharmaceutical arts have been attempting to focus on the problem of bone loss in older patients, particularly post-menopausal women. It has been shown that there is a relationship between estrogen activity and the prevention or even reversal of such bone loss, but the problem is by no means solved at the present time.

SUMMARY OF THE INVENTION

This invention provides 11-(substituted phenyl)-11H-benzo[a]fluorenes of the formula

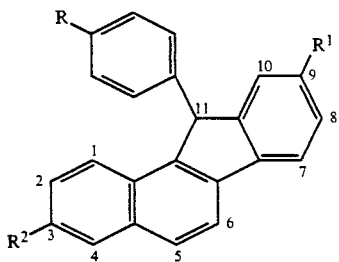

I wherein R represents hydroxy or $-O-(CH_2)_nN(R^3)(R^4)$; $R^1$ represents hydrogen, hydroxy, $C_1-C_3$ alkoxy, halo, or $-COR^5$; $R^2$ represents hydrogen, hydroxy, $C_1-C_3$ alkoxy, or $-COR^5$; n represents 1-3; $R^3$ and $R^4$ independently represent $C_1-C_4$ n- or sec-alkyl; or $R^3$ and $R^4$ combine to represent butylene, pentylene or hexylene; $R^5$ represents $C_1-C_5$ alkyl, phenyl, or phenyl substituted with 1 or 2 groups chosen from halo, $C_1-C_3$ alkyl, hydroxy, and $C_1-C_3$ alkoxy; and the physiologically acceptable acid addition salts thereof.

The compounds have estrogenic and anti-estrogenic activity, and are used as pharmaceuticals for anti-estrogen therapy, anti-fertility therapy, antineoplastic therapy, and the prevention of bone loss. Accordingly, pharmaceutical compositions and such methods of therapy are important parts of the invention. Such methods of therapy comprise the administration of an effective dose of a compound described above to a subject suffering from such a condition or at risk of suffering from such a condition.

DESCRIPTION OF THE PREFERRED EMBODIMENTS

This invention provides a series of new pharmaceutical compounds, and the physiologically acceptable salts thereof. Certain compounds of the invention constitute preferred aspects thereof. For example, the compounds wherein R is hydroxy are preferred as intermediates, and the compounds wherein R is substituted-aminoalkoxy are preferred as pharmaceuticals. Certain other classes of the compounds are preferred for various reasons. The following paragraphs describe such preferred classes; it will be understood that the classes may be combined to form additional, further preferred classes.
a. $R^1$ is hydrogen, hydroxy, or alkoxy;
b. $R^1$ is hydrogen or hydroxy;
c. $R^2$ is hydrogen, hydroxy, or alkoxy;
d. $R^2$ is hydrogen or hydroxy;
e. n is 2;
f. $R^3$ and $R^4$ are butylene, pentylene or hexylene;
g. $R^3$ and $R^4$ independently are $C_1-C_4$ n- or sec- alkyl;
h. $R^3$ and $R^4$ independently are methyl or ethyl;
i. $R^3$ and $R^4$ independently are $C_1-C_3$ n-alkyl;
j. $R^5$ is alkyl or phenyl;
k. $R^5$ is $C_1-C_3$ alkyl or phenyl.

In the above general and preferred descriptions of the compounds, the general chemical terms have their usual meaning, but some exemplification of the terms will be given to assure clarity. For example, the term $C_1-C_3$ alkoxy includes methoxy, ethoxy, n-propoxy and isopropoxy. The term halo includes iodo, bromo, chloro and fluoro.

The term n in the definition of R is 1-3, so that the alkylene spacer group in that group is methylene, ethylene or n-propylene. The groups $R^3$ and $R^4$ in the R group can combine to form a polymethylene group, so that the total group $-N(R^3)(R^4)$ may represent pyrrolidino, piperidino, or hexamethyleneimino. Alternatively, $R^3$ and $R^4$ may represent $C_1-C_4$ normal or secondary alkyl, so that each of the groups may represent independently methyl, ethyl, n-propyl, isopropyl, n-butyl or isobutyl. Preferably, those groups may represent $C_1-C_3$ normal alkyl or methyl or ethyl, in various preferred embodiments.

It will be understood that $-N(R^3)(R^4)$ may thus represent groups such as dimethylamino, ethylmethylamino, di-n-propyl amino, n-butylethylamino, isobutylisopropylamino and the like.

The group $R^5$ can represent $C_1-C_5$ alkyl, including groups such as methyl, isopropyl, t-butyl, n-butyl, pentyl, 2-methylbutyl and the like. The group may also represent phenyl which may be substituted with 1 or 2 groups as defined above to provide substituted phenyl groups such as 4-chlorophenyl, 2-iodo-3-n-propylphenyl, 3-hydroxy-4-propoxyphenyl, 2,6-dihydroxyphenyl, 4-isopropoxy-2-iodophenyl and the like.

In order to assure that the reader fully understands the compounds of the present invention, a group of representative members of the genus will be named.
9-ethoxy-11-[4-(2-hexamethyleneimin-1-ylmethoxy)-phenyl]-11H-benzo[a]fluorene
3-(hydroxy-9-isopropoxy-11-[4-(3-isobutylmethylaminopropoxy)phenyl]-11H-benzo[a]fluorene
9-chloro-3-ethoxy-11-[4-(2-isopropylpropylaminoethoxy)phenyl]-11H-benzo[a]fluorene
3,9-bis(acetyl)-11-[4-(2-di-n-butylaminoethoxy)phenyl]-11H-benzo[a]fluorene 3-chloro-9-fluoro-11-[4-(ethylisopropylaminomethoxy)-phenyl]-11H-benzo[a]fluorene 9-butyryl-3-ethoxy-11-[4-(2-di-n-propylaminoethoxy)-phenyl]-11H-benzo[a]fluorene 9-bromo-3-n-pentanoyl-11-[4-(3-ethylmethylaminopropoxy)phenyl]-11H-benzo[a]fluorene 3-fluoro-9-pivaloyl-11-[4-(2-pyrrolidin-1-ylethoxy)-phenyl]11H-benzo[a]fluorene 9-iodo-3-propionyl-11-[4-(2-piperidin-1-ylethoxy)-phenyl]-11H-benzo[a]fluorene 3-methoxy-9-hexanoyl-11-[4-(2-diethylaminoethoxy)-phenyl]-11H-benzo[a]fluorene 3-(2,4-dichlorobenzoyl)-11-(4-hydroxyphenyl)-9-benzoyl-11H-benzo[a]fluorene 3-bromo-9-(2-fluorobenzoyl)-11-(4-hydroxyphenyl)-11H-benzo[a]fluorene 3-acetyl-11-(4-hydroxyphenyl)-9-(2,6-dimethylbenzoyl)-11H-benzo[a]fluorene 3-hydroxy-11-(4-hydroxyphenyl)-9-(4-propoxybenzoyl)-11H-benzo[a]fluorene 11-(4-hydroxyphenyl)-9-[3,5-bis(methoxybenzoyl]-11H-benzo[a]fluorene 11-(4-hydroxyphenyl)-9-(4-hydroxybenzoyl)-11H-benzo[a]fluorene 3-hydroxy-11-(4-hydroxyphenyl)-9-(3-bromo-4-propyl-benzoyl)-11H-benzo[a]fluorene 9-hydroxy-11-(4-hydroxyphenyl)-3-(1-methyl-propionyl)-11H-benzo[a]fluorene 3-(4-bromo-3-ethylbenzoyl)-11-(4-hydroxyphenyl)-11H-benzo[a]fluorene 11-(4-hydroxyphenyl)-3-iodo-9-propoxy-11H-benzo[a]fluorene It will be understood that the present compounds have an asymmetric center, and accordingly exist as pairs of enantiomers. This invention contemplates the use of either enantiomer, or a mixture of both enantiomers.

The physiologically acceptable acid addition salts of the aminoalkoxy compounds of the present invention include those which are often used in pharmaceutical chemistry. For example, such salts may be formed with inorganic or organic acids such as hydrobromic acid, hydriodic acid, sulfonic acids including such agents as naphthylenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferably with hydrochloric acid, methanesulfonic acid, maleic acid, acetic acid or propionic acid. It is frequently advantageous to administer such a compound in the form of an acid addition salt.

The compounds of the present invention are conveniently made from 3-phenyl-4-benzoyl-1,2-dihydronaphthalenes, such as are taught in U.S. Pat. No. 4,230,862 of Suarez and Jones. That patent teaches the synthesis of such compounds having most of the substituents corresponding to $R^1$ and $R^2$ of the present compounds of formula I. The rest of the needed intermediates are readily obtained by syntheses analogous to those which Suarez and Jones teach. The dihydronaphthalene, preferably having a 4-hydroxy group on the phenyl ring, is cyclized, as by a strongly acid reagent at moderate temperatures. Methanesulfonic acid is a conventient cyclizing agent; so is hydrobromic acid and other strong acids such as sulfuric, perchloric, fluoroboric, hydrochloric, alkane sulfonic, phosphoric, polyphosphoric and the like.

The cyclizations are readily carried out at ambient temperature or temperatures in the range of from about 0° C. to about 50° C. Methanesulfonic acid is preferably used neat, although it can be used in the presence of inert solvents such as chloroform, 1,2-dichloroethane, methylene chloride, ethyl acetate, $CH_3CN$, dioxane, and the like.

Hydrobromic acid is preferably used as an aqueous solution containing a concentration in the range of about 30–70% HBr.

The cyclization, when carried out on an appropriately chosen dihydronaphthalene, provides the desired compound of formula I wherein R is hydroxy. The pharmaceutical aminoalkoxy compounds are obtained by a simple alkylation of the hydroxy group of that intermediate compound with the appropriate aminoalkyl reagent. It is preferred to use a reagent having a good leaving group, such as chloro, bromo, or an alkyl sulfonate, at the terminal carbon of the alkyl group, and to carry out the alkylation in the presence of an acid scavenger. Inorganic bases such as sodium or potassium carbonate or hydroxide are particularly convenient acid scavengers, but strong organic bases such as sodium hydride, potassium hydride, sodium amide, lithium diisopropyl amide and the like may conveniently be used as well. The reaction goes best at high temperature, and so it is preferred to carry the reaction out in high-boiling solvents, such as dimethylformamide or dimethylacetamide, and to carry the reaction out for a few hours at temperatures in the range of from about 100° to about 200° C.

In some cases, it is convenient to modify the $R^1$ and $R^2$ groups as final steps in the synthesis. For example, when hydroxy groups are desired at those positions, it may be convenient to obtain such compounds by dealkylating the corresponding methoxy or ethoxy intermediates. The examples below demonstrate such syntheses.

Dealkylations can be carried out, for example, with aluminum chloride and ethanethiol at low temperatures in the range of from, for example, about -20° C. to about ambient temperature.

The salts may be conveniently formed, as is usual in organic chemistry, by simply reacting an aminoalkoxy compound of the present invention with the appropriate acid, such as have been described above. The reaction may be carried out in an appropriate solvent, such as acetone, an alcohol, an aromatic solvent or the like. The salts are quickly formed in high yields at moderate temperatures, and often may be prepared by merely isolating the compound from a suitable acidic wash as the final step of the synthesis. On the other hand, when the compound of this invention is desired in the free base form, the examples below show how conveniently the compounds may be isolated from organic reaction media, or from a basic final wash according to the usual practice of organic chemists.

The following examples are provided further to assist the reader in understanding the synthesis of the various compounds of formula I.

EXAMPLE 1

11-(4-hydroxyphenyl)-9-methoxy-11H-benzo[a]fluorene

A 15 g portion of 4-(4-hydroxybenzoyl)-3-(4-methoxyphenyl)-1,2-dihydronaphthalene was dissolved in 200 g of methanesulfonic acid under nitrogen, and was stirred overnight at ambient temperature. Then the suspension was poured over 200 g of ice and the mixture was added to 100 ml of brine, which was in turn extracted with 300 ml of ethyl acetate. The organic extract was then washed with 100 ml of water, with 100 ml of saturated aqueous sodium bicarbonate solution, and again with 20 ml of brine. The organic extract was concentrated and the residue was digested with hot isopropanol. The digestion mixture was cooled overnight to obtain 3.2 g of the desired product. That product was recrystallized from ethyl acetate to obtain 2.74 g of the desired product in pure form. The product was identified by its field desorption mass spectrum m/e 338 (calc'd m/e 338) and its NMR spectrum.

NMR (DMSO-$d_6$)δ 3.70 (s, 3, OCH$_3$), 5.80 (s, 1, CH), 6.6 to 8.1 (m, 13, aromatic), 9.30 (s, 1, OH).

Analysis calc.: C, 85.18; H, 5.36. Found: C, 85.29; H, 5.43.

EXAMPLE 2

11-(4-hydroxyphenyl)-3-methoxy-11H-benzo[a]fluorene

A 17.4 g portion of 3-(4-hydroxybenzoyl)-3-methoxy-4-phenyl-1,2-dihydroxynaphthalene was dissolved in 120 ml of methanesulfonic acid and was stirred at ambient temperature overnight. The product was extracted as described in Example 1, and it was subsequently purified by chromatography over silica gel, eluting with a gradient solvent changing from hexane to 30% ethyl acetate in hexane. The product-containing fractions were concentrated under vacuum, and the product was taken up in isopropanol, recrystallized and washed with hexane to obtain 12.8 g of the desired product. Field desorption mass spectrum m/e 388 (calc'd m/e 388).

NMR (CDCl$_3$)δ 4.73 (s, 1, OH), 3.92 (s, 3, OCH$_3$), 5.25 (s, 1, CH), 6.6 to 8.0 (m, 13, aromatic).

Analysis calc.: C, 85.18; H, 5.36. Found: C, 84.95; H, 5.58.

EXAMPLE 3

11-(4-hydroxyphenyl)-3,9-bis(methoxy)-11H-benzo[a]fluorene

A 8.4 g portion of 4-(4-hydroxybenzoyl)-6-methoxy-3-(4-methoxyphenyl)-1,2-dihydronaphthalene was added to 90 ml of methanesulfonic acid, and the mixture was stirred under nitrogen for 3 days. The mixture was then poured into 200 ml of brine, and was extracted 3 times with 200 ml portions of ethyl acetate. The organic extract was dried over magnesium sulfate, filtered and evaporated under vacuum to a dark oil. The impure product was purified by Waters Prep 500 liquid chromatography over silica gel, using a gradient solvent from 3.5 liters of toluene to 3.5 liters of 10% ethyl acetate in toluene. Fractions (200 ml each) were collected, and fractions 11-13 contained the product, which was isolated by concentration of the solvent under vacuum. The residual oily tan crystals were recrystallized from 30 ml of isopropanol and recrystallized to obtain 1.81 g of purified product, m.p. 196°-199° C.

NMR (DMSO-$d_6$) δ 3.72 (s, 3, OCH$_3$), 3.82 (s, 3, OCH$_3$), 5.31 (s, 1, CH), 6.6 to 7.0 (m, 12, aromatic), 9.24 (s, 1, OH).

Analysis calc.: C, 81.50; H, 5.47. Found: C, 81.52; H, 5.69.

EXAMPLE 4

9-methoxy-11-[4-(dimethylaminoethoxy)phenyl]-11H-benzo[a]fluorene

A 3.4 g portion of the compound of Example 1 was combined with 75 ml of methyl ethyl ketone, 6.1 g of potassium carbonate, and 2.45 g of dimethyl-(2-chloroethyl)amine hydrochloride. The mixture was stirred under reflux for 24 hours. After cooling to 25° C., 50 g of ice and 100 ml of ethyl acetate were added. The organic layer was separated, washed with brine, and concentrated to provide the crude product which was then purified on a silica gel column (120 mm high and 70 mm in diameter). The elution started with 500 ml of toluene, and proceeded through 300 ml increments of toluene containing from 1 to 10% triethylamine, in 1% increments. The product-containing fractions were combined and concentrated to dryness under vacuum to obtain 3.1 g of partially purified product, which was chromatographed again on a similar column, beginning with 100 ml of toluene. The gradient solvent was then changed in 100 ml increments from toluene containing 10% of 5:3 ethyl acetate:acetonitrile, to 10% of toluene in the ethyl acetate:acetonitrile mixture. Then a second gradient solvent was used, again in 100 ml increments, starting with the 5:3 ethyl acetate:acetonitrile mixture, going to the same solvent containing 10% of triethylamine. The product-containing fractions were then evaporated under vacuum to obtain 2.9 g of purified desired product, m.p. 159°-160° C.

NMR (CDCl$_3$) δ 2.29 (s, 6, N-CH$_3$); 2.65 (t, 2, NCH$_2$CO), 3.80 (s, 3, OCH$_3$), 3.96 (t, 2, NCCH$_2$), 5.25 (s, 1, CH), 6.7 to 8.0 (m, 13, aromatic).

Analysis calc.: C, 82.12; H, 6.65; N, 3.42.
Found: C, 81.89; H, 6.41; N, 3.36.

EXAMPLE 5

9-methoxy-11-[4-(2-diethylaminoethoxy)phenyl]-11H-benzo[a]fluorene

Seven grams of the product of Example 1 was combined with 5.7 g of diethyl-(2-chloroethyl)amine hydrochloride and 12.1 g of potassium carbonate in 75 ml of methyl ethyl ketone, and the mixture was stirred under reflux for 3½ hours. The mixture was then poured into ice water, extracted twice with 300 ml portions of ethyl acetate, and the organic extract was washed with brine, dried, and evaporated under vacuum to a tan liquid. The impure product was purified by chromatography over a silica gel column, eluting with a gradient solvent beginning with 200 ml of toluene, then proceeding in 200 ml increments to 100% ethyl acetate, and finally eluting with 500 ml of 1:9 methanol:ethyl acetate. The product-containing fractions were evaporated under vacuum to obtain 3.85 g of the desired product, m.p. 109°-115° C.

NMR (CDCl$_3$) δ 1.01 (t, 6, C-CH$_3$), 2.57 (t, 2, NCH$_2$CO), 2.82 (t, CH$_2$-C), 3.81 (s, 3, OCH$_3$), 3.99 (t, 2, NCCH$_2$), 5.28 (s, 1, CH), 6.7 to 8.0 (m, 13, aromatic).

Analysis calc.: C, 82.35; H, 7.14; N, 3.20.
Found: C, 82.46; H, 6.91; N, 3.12.

EXAMPLE 6

9-methoxy-11-[4-(2-piperidin-1-ylethoxy)phenyl]-11H-benzo[a]fluorene

Five g of the compound of Example 1 was combined with 10.9 g of potassium carbonate, 50 ml of dimethylformamide, and 2.9 g of 1-(2-chloroethyl)piperdine hydrochloride. The mixture was stirred under reflux for 1 hour under nitrogen, and it was then cooled and poured into 1500 ml of iced brine. The aqueous mixture was extracted 3 times with 200 ml portions of ethyl acetate, and the organic extract was washed 3 times with 25 ml portions of brine, dried and evaporated under vacuum to obtain 6.6 g of tan crystals. The impure product was purified by high performance liquid chromatography over silica gel, using 2% triethylamine and diethyl ether. The product-containing fractions were concentrated under vacuum to obtain 5.43 g of white crystals, which were recrystallized from 60 ml of acetone to obtain 3.95 g of pure product, m.p. 147°–148° C.

NMR (DMSO-$d_6$) δ 1.33 (br m, 2, 4-$CH_2$ group of piperidine ring), 1.45 (br m, 4, 3-$CH_2$ groups of piperidine ring), 2.40 (br m, 4, 2-$CH_2$ groups of piperidine ring), 2.60 (t, 2, $NCH_2CO$), 3.27 (s, 3, $OCH_3$), 3.76 (s, 3, $OCH_3$), 3.98 (t, 2, $NCCH_2$), 5.45 (s, 1, CH), 6.8 to 8.1 (m, 13, aromatic).

Analysis calc.: C, 82.82; H, 6.95; N, 3.12. Found: C, 82.58; H, 6.66; N, 3.09.

EXAMPLE 7

9-methoxy-11-[4-(2-hexamethyleneimino-1-ylethoxy)-phenyl]-11H-benzo[a]fluorene

Seven g of the compound of Example 1 was combined with 75 ml of methyl ethyl ketone, 12.2 g of potassium carbonate and 6.54 g of 1-(2-chloroethyl)hexamethyleneimine hydrochloride. The mixture was stirred under reflux for 96 hours, and was then cooled and poured into ice-water. The aqueous mixture was extracted twice with 200 ml portions of ethyl acetate, and the organic extract was washed with brine, dried and evaporated down to a honey-colored oil. The impure product was chromatographed over silica gel, using a gradient solvent from toluene to ethyl acetate. The appropriate fractions were combined and evaporated under vacuum to obtain 2.1 g of product, m.p. 124°–126° C.

NMR (CDCl$_3$) δ 1.58 (br m, 6, C-($CH_2$)$_3$-C of hexamethyleneimine ring), 2.75 (br m, 4, $CH_2$-N groups of hexamethyleneimine ring), 2.83 (t, 2, $NCH_2CO$), 3.78 (s, 3, $OCH_3$), 3.98 (t, 2, $NCCH_2$), 5.20 (s, 1, CH), 6.7 to 7.9 (m, 13, aromatic).

Analysis calc.: C, 82.90; H, 7.17; N, 3.02. Found: C, 82.68; H, 6.89; N, 2.95.

EXAMPLE 8

9-methoxy-11-[4-(2-bis(isopropyl)aminoethoxy)-phenyl]-11H-benzo[a]fluorene

A 7 g portion of the compound of Example 1 was reacted with 6.6 g of 2-chloroethyl-bis(isopropyl)amine hydrochloride in the presence of 12.2 g of potassium carbonate in 75 ml of methyl ethyl ketone. The mixture was stirred under reflux for 72 hours, and was then worked up as described in Example 5. The impure product was chromatographed over silica gel with a gradient solvent proceeding from toluene to 9:1 toluene:ethyl acetate. Concentration of the product-containing fractions gave 4.16 g of the desired product, m.p. 106°–115° C.

NMR (CDCl$_3$) δ 1.01 (d, 12, $CH_3$-C), 2.5 to 3.3 (br m, 4, CH-C groups and $NCH_2CO$), 3.81 (s, 3, $OCH_3$), 3.92 (t, 2, $NCCH_2$), 5.23 (s, 1, CH), 6.7 to 7.9 (m, 13, aromatic).

Analysis calc.: C, 82.54; H, 7.58; N, 3.01. Found: C, 82.72; H, 7.55; N, 3.14.

EXAMPLE 9

9-methoxy-11-[4-(2-pyrrolidin-1-ylethoxy)phenyl]-11H-benzo[a]fluorene

A 7 g portion of the compound of Example 1 was dissolved in 100 ml of dry dimethylformamide, and to it was added 1.05 g of 50% mineral oil dispersion of sodium hydride and 4 g of 1-(2-chloroethyl)pyrrolidine. The mixture was then stirred at 60° C. for 3 hours and cooled. It was then poured over 500 ml of ice and water, and the mixture was extracted 3 times with 250 ml portions of ethyl acetate. The organic extract was washed with two 50 ml portions of brine, dried and concentrated under vacuum. The residue was chromatographed over a 5 cm×50 cm silica gel column with 3:1 ethyl acetate:toluene, followed by ethyl acetate. The product-containing fractions were combined and concentrated under vacuum to contain 4.5 g of the title compound.

NMR (DMSO-$d_6$) δ 1.75 (br m, 4, C-($CH_2$)$_2$-C of pyrrolidine ring), 2.50 (br m, 4, $CH_2$-N groups of pyrrolidine ring), 2.78 (t, 2, $NCH_2CO$), 3.70 (s, 3, $OCH_3$), 3.96 (t, 2, $NCCH_2$), 5.13 (s, 1, CH), 6.7 to 7.9 (m, 13, aromatic).

Analysis calc.: C, 82.73; H, 6.71; O, 7.35; N, 3.23. Found: C, 82.37; H, 7.03; O, 7.57; N, 3.40.

EXAMPLE 10

9-methoxy-11-[4-(2-pyrrolidin-1-ylethoxy)phenyl]-11H-benzo[a]fluorene, methanesulfonate A solution of 657 mg of the compound of Example 9 in 10 ml of acetone was combined with 141 mg of methanesulfonic acid, and the mixture was briefly swirled. The acetone was then evaporated under vacuum, and the oily residue was triturated with methyl ethyl ketone. The trituration mixture was allowed to stand overnight, during which time the desired salt crystallized. The solid was separated and recrystallized from fresh methyl ethyl ketone to obtain the desired product, m.p. 161°–162.5° C.

NMR (CDCl$_3$) δ 2.00 (br m, 4, C-($CH_2$)$_2$C of pyrrolidine), 2.70 (s, 3, $CH_3$-S), 2.90 (br m, 4, $CH_2$-N groups of pyrrolidine ring), 3.40 (t, 2, $NCCH_2$), 3.81 (s, 3, $OCH_3$), 4.30 (t, 2, $NCH_2CO$), 5.20 (s, 1, CH), 6.6 to 8.0 (m, 13, aromatic), 11.10 (br s, 1, N-H).

Analysis calc.: C, 70.03; H, 6.26; N, 2.63; O, 15.05; S, 6.03. Found: C, 69.79; H, 6.03; N, 2.51; O, 15.30; S, 5.86.

EXAMPLE 11

3,9-bis(methoxy)-11-[4-(2-piperidin-1-ylethoxy)-phenyl]-11H-benzo[a]fluorene

A 1.8 g portion of the compound of Example 3 was combined with 3.4 g of potassium carbonate, 0.95 g of 1-(2-chloroethyl)piperidine hydrochloride and 20 ml of dimethylformamide, and the reaction was carried out and the product was isolated as described above in Example 6. The chromatography gave 2.05 g of purified product, which was recrystallized from ethyl acetate/isooctane to obtain 1.93 g of highly purified product, m.p. 162°–164° C.

NMR (DMSO-$d_6$) δ 1.33 (br m, 2, 4-$CH_2$ of piperidine ring), 1.45 (br m, 4, 3-$CH_2$ groups of piperidine ring), 2.36 (br m, 4, 2-$CH_2$ groups of piperidine ring), 2.57 (t, 2, $NCH_2CO$), 3.70 (s, 3, $OCH_3$), 3.81 (s, 3, OCH₃), 3.94 (t, 2, NCCH₂), 5.38 (s, 1, CH), 6.7 to 8.0 (m, 12, aromatic).

Analysis calc.: C, 80.14; H, 6.74; N, 2.92. Found: C, 79.87; H, 6.77; N, 2.81.

EXAMPLE 12

3-methoxy-11-[4-(2-piperidin-1-ylethoxy)phenyl]-11H-benzo[a]fluorene

Eight g of the compound of Example 2 was combined with 16.3 g of potassium carbonate and 4.6 g of 1-(2-chloroethyl)piperidine hydrochloride in 75 ml of dimethylformamide under anhydrous conditions, and the process was carried out and the product isolated as described in Example 6 above. The 9.5 g of product from the chromatography was recrystallized from isopropanol to obtain 8.74 g of the desired product, m.p. 130°–133° C.

NMR (CDCl₃) δ 1.42 (br m, 2, 4-CH₂ of piperidine ring), 1.60 (br m, 4, 3-CH₂ groups of piperidine ring), 2.45 (br m, 4, 2-CH₂ groups of piperidine ring), 2.75 (t, 2, NCH₂CO), 3.90 (s, 3, OCH₃), 4.02 (t, 2, NCCH₂), 5.25 (s, 1, CH), 6.7 to 8.0 (m, 13, aromatic).

Analysis calc.: C, 82.82; H, 6.95; N, 3.12. Found: C, 82.82; H, 7.10; N, 3.08.

EXAMPLE 13

9-hydroxy-11-[4-(2-piperidin-1-ylethoxy)phenyl]-11H-benzo[a]fluorene

Four g of the compound of Example 6 was added to a suspension of 8.3 g of aluminum chloride and 5.5 g of ethanethiol in 100 ml of 1,2-dichloroethane. The mixture was initially stirred at 0° C. for 1 hour, and it was then allowed to warm to ambient temperature and stirred overnight. The reaction was cooled to 0° C. and 100 ml of tetrahydrofuran was added. Then the reaction was poured over a mixture of ice (200 ml), water (500 ml) and concentrated hydrochloric acid (10 ml). After thorough mixing, the acidic mixture was basified by the cautious addition of excess solid NaHCO₃. The resulting basic mixture was extracted with 3×100 ml of ethyl acetate. The extracts were dried over anhydrous MgSO₄, filtered and concentrated to obtain 4.5 g of the desired product, which was purified by recrystallization from acetone to obtain 2.08 g of the desired product, m.p. 180°–181° C., as off-white crystals. A sample was recrystallized a second time from acetone.

NMR (CDCl₃) δ 1.42 (br m, 2, 4-CH₂ of piperidine ring), 1.60 (br m, 4, 3-CH₂ groups of piperidine ring), 2.52 (br m, 4, 2-CH₂ groups of piperidine ring), 2.73 (t, 2, NCH₂CO), 3.90 (t, 2, NCCH₂), 5.19 (s, 1, CH), 6.5 to 7.9 (m, 15, aromatic and —OH).

Analysis calc.: C, 82.73; H, 6.71; N, 3.22. Found: C, 82.94; H, 6.55; N, 3.16.

EXAMPLE 14

3-hydroxy-11-[4-(2-piperidin-1-ylethoxy)phenyl]-11H-benzo[a]fluorene

Two g of the compound of Example 12 was added to a suspension of 4.2 g of aluminum chloride and 2.8 g of ethanethiol in 50 ml of 1,2-dichloroethane at 0° C. The mixture was stirred for 2.5 hours at 0° C., and then worked up by the procedure used in Example 13. Thereby there was obtained 2.0 g of crystalline product. The product was recrystallized from acetone to obtain 1.71 g of the desired product, m.p. 216°–217° C.

NMR DMSO-d₆) δ 1.35 (br m, 2, 4-CH₂ of piperidine ring), 1.47 (br m, 4, 3-CH₂ groups of piperidine ring), 2.40 (br m, 4, 2-CH₂ groups of piperidine ring), 2.60 (t, 2, NCH₂CO), 3.98 (t, 2, NCCH₂), 5.43 (s, 1, CH), 6.8 to 8.1 (m, 13, aromatic), 9.75 (s, 1, OH).

Analysis calc.: C, 82.73; H, 6.71; N, 3.22. Found: C, 82.72; H, 6.68; N, 3.19.

Field Desorption mass spectrum m/e 436 (M+1).

EXAMPLE 15

3,9-dihydroxy-11-[4-(2-piperidin-1-ylethoxy)-phenyl]-11H-benzo[a]fluorene

One g of the compound of Example 11 was added to 1.9 g of aluminum chloride and 1.3 g of ethanethiol in 25 ml of 1,2-dichloroethane and the reaction was carried out and the product isolated as described in Example 14. One g of impure oily product was obtained, which was purified by Waters Prep 500 liquid chromatography over normal phase silica gel, using a gradient solvent which began with 2% methanol in chloroform and progressed to 30% methanol in chloroform. The product-containing fractions were evaporated to dryness under vacuum to obtain 0.7 g of the desired product as a tan foam.

NMR (DMSO-d₆) δ 1.35 (br m, 2, 4-CH₂ of piperidine ring), 1.45 (br m, 4, 3-CH₂ groups of piperidine ring), 2.40 (br m, 4, 2-CH₂ groups of piperidine ring), 2.60 (t, 2, NCH₂CO), 3.96 (t, 2, NCCH₂), 5.30 (s, 1, CH), 6.6 to 7.9 (m, 12, aromatic), 9.30 (s, 1, OH), 9.61 (s, 1, OH).

Analysis calc.: C, 79.80; H, 6.47; N, 3.10. Found: C, 79.63; H, 6.43; N, 3.17.

Field desorption mass spectrum for Example 15: m/e 452 (M+1).

BIOLOGICAL ACTIVITY

Test I

Estrogenic Activity

The first test reported below was used to determine the estrogenic potency of the compounds.

The test was conducted with adult ovariectomized female Sprague Dawley strain rats weighing 225–275 g. Compounds to be tested were prepared for daily subcutaneous or oral administration in 0.1 ml of corn oil per dose. Each control or treated group consisted of 5 animals. The animals were treated daily for seven days.

Two parameters of estrogenic activity were determined. The degree of estrogenic response attained in vaginal cytology was scored by microscopic examination of daily vaginal smears. No change in cell shedding was scored as 0, a predominant active shedding of rounded epithelial cells was scored as 2 and predominant heavy shedding of cornified cells was scored as 3. On the eighth day the animals were sacrificed with carbon dioxide and estrogenic activity was also determined by comparing the uterine weight of treated animals to that of control animals. The results were as follows.

| Test I ESTROGENIC RESPONSE TEST | | | |
|---|---|---|---|
| Compound of Example No. | Dose | Uterine Wt. | Vaginal Score |
| Control | | 106 mg | 0 |
| 4 | 0.1 mg sc | 201 mg | 2— |
| 5 | 0.1 mg sc | 160 mg | 2— |
| 6 | 0.1 mg sc | 176 mg | 2 |
| 7 | 0.1 mg sc | 189 mg | 2 |
| 8 | 0.1 mg sc | 190 mg | 2 |

-continued

| Test I ESTROGENIC RESPONSE TEST | | | |
|---|---|---|---|
| Compound of Example No. | Dose | Uterine Wt. | Vaginal Score |
| 9 | 0.1 mg sc | 197 mg | 1– |
| 9 | 0.1 mg oral | 188 mg | 2 |
| 10 | 0.1 mg sc | 180 mg | 2 |

Test II

Antiestrogenic Response Test

This test was carried out substantially as was Test 1, except that estradiol, 0.3 μg/rat/day, was administered subcutaneously as the uterotrophic control and to the test groups which were treated additionally with the compounds of the present invention. All compounds were administered subcutaneously in this test. Vaginal scores were measured as described in test 1, and the animals were sacrificed on the eighth day and the uterine weights were measured in order to determine the antiestrogenic activity of the compounds by comparing the uterine weights of the treated animals to those of animals treated with estradiol alone. Results are shown in the following table.

| Test II ANTIESTROGENIC RESPONSE TEST | | | |
|---|---|---|---|
| Compound of Example No. | Dose (mg) | Uterine Wt. (mg) | Vaginal Score |
| Control | | 110 | 0 |
| Estradiol | | 273 | 3 |
| Extradiol | | | |
| +4 | .01 | 207 | 3 |
| +5 | .01 | 193 | 2– |
| +6 | .01 | 196 | 2– |
| +7 | .01 | 230 | 3 |
| +8 | .01 | 224 | 3 |
| +9 | .01 | 216 | 2 |
| +9 | .005 | 189 | 3 |
| +10 | .01 | 213 | 3 |

Test III

Antifertility Test

Virgin female Sprague Dawley rats weighing 225-300 g were housed with breeder males of the same strain. The day following breeding was designated day 1 of each experiment, and was the first day of treatment. The compounds for testing were prepared in 0.1 ml/dose of corn oil, and compounds were administered (subcutaneously or orally) daily for 11 days, starting with day 1. On the twelfth day the animals were sacrificed with carbon dioxide, and the uteri were removed and examined for the presence of viable or resorbing implantation sites. Each treatment or control group consisted of 5 animals each. Control rats cohabited and monitored in this way have a fecundity rate very close to 100%.

In the following table, the observations are reported as the implantation ratio, which reports the number of animals with implantation sites per group of five animals. In the control groups, this ratio is substantially always 5/5. The number of viable and resorbing implantation sites per animal is also reported as a ratio, viable/resorbing. In the control groups, this ratio ranges from 6/0 to 14/0.

| Test III ANTIFERTILITY ACTIVITY | | | | |
|---|---|---|---|---|
| Compound of Ex. No. | Dose (mg) | Route | Implant. Ratio | Viable/ Resorbing |
| 4 | .05 | sc | 0/5 | 0/0 |
| | .01 | sc | 1/5 | 2.2/0 |
| 5 | .01 | sc | 0/5 | 0/0 |
| 6 | .05 | sc | 0/5 | 0/0 |
| | .01 | sc | 3/5 | 4.8/0.2 |
| 7 | .01 | sc | 2/5 | 2.4/0 |
| | .001 | sc | 5/5 | 11.8/0 |
| 8 | .05 | sc | 3/5 | 2.4/3.8 |
| 9 | .005 | or | 0/5 | 0/0 |
| 10 | .001 | sc | 5/5 | 12.4/0 |
| | .05 | sc | 0/5 | 0/0 |
| | .01 | sc | 4/5 | 8/0 |

Test IV

Bone Loss Test

Female rats, 75 days old, were obtained from Charles River Laboratories, and housed in groups of 3. After acclimatization to the laboratory, the rats were ovariectomized, and treatment with daily doses of the test compound was begun the day of surgery. The animals were dosed every day for 35 days, and were then decapitated. The right femur of each animal was excised, and each femur was scanned 3 times at the distal metaphysis, 1 mm from the patellar groove, by single photon absorptiometry. The instrument used was a digital bone densitometer manufactured by Norland Corp., Fort Atkinson, Wis., which uses $^{125}$iodine as a radiation source.

In typical experiments, intact animals show a bone density of 0.24 to 0.27 g/cm/cm. Ovariectomized control animals exhibit a density of about 0.16 to about 0.19 g/cm/cm.

In experiment 1, the compound of Example 12 was administered at doses from 0.01 mg/day to 10 mg/day, and was found to increase femur density to about 0.22 to about 0.24 g/cm/cm when administered orally. In that test, the compound prevented about 50% of the bone loss resulting from ovariectomy, about the same as treatment with estradiol.

In another experiment, the compound of Example 12 was administered subcutaneously at doses from 0.01 to 50 mg/kg, and the maximal effect was found at 0.1 mg/kg, where about 25% of the bone loss was prevented, again, about the same result as attained by estradiol. At the highest doses in the experiment, the observed bone loss was worse than in the control ovariectomized animals.

In a third experiment, the same compound was administered at from 0.01 to 10 mg/kg, both orally and subcutaneously, and the best results were attained by oral administration at 10 mg/kg, where approximately 60% of the bone loss was prevented. Estradiol in this test, however, prevented about 85% of the bone loss. The best effect seen following subcutaneous administration of the compound in that test was found at the 0.1 mg/kg dose level, where about 40% of the bone loss was prevented.

Test V

Antitumor Test

Mammary tumors were induced in adult female rats by a single 20 mg oral dose of 7, 12-dimethylbenzanthracene. Within about 6 weeks, visible and palpable tumors were present in the mammary tissue of the rats, and the rats were allocated into treatment and control groups in such a way that each group contained animals having approximately the same size and number of tumors. The size of the tumors was estimated by measuring their cross-sectional area. Each animal in the treatment groups was given a daily dose of 0.2 ml of corn oil containing the test compound, that of Example 12, and the control animals were given corn oil. In one experiment, in which the compound was administered at 30 mg/kg/day, after 4 weeks of treatment, the control animals had tumors averaging 1176 square millimeters, and the animals which received the test compound had tumors averaging 7.1 square millimeters.

In a second experiment, the compound of Example 12 was administered at 5, 15, and 30 mg/kg/day, and the control animals had tumors averaging 836 square millimeters. The 3 treatment groups of animals had tumors averaging 223, 84 and 179 square millimeters, respectively. However, one animal in the 30 mg/kg group had a quite unusually large and fast-growing tumor, so that result is somewhat skewed.

The foregoing experiments show clearly that the representative compounds of this invention have pronounced estrogenic and anti-estrogenic activity, and that they are accordingly useful for antitumor, antifertility and bone replacement therapy which follow from the estrogenic and anti-estrogenic effects.

Accordingly, the present invention provides a method of contributing an estrogenic or anti-estrogenic effect to a subject in need of such therapy which comprises administering an effective dose of a compound of formula 1 to such subject. Use in human subjects is preferred.

The dose of a compound of the present invention to be administered to a subject is widely variable. It should be noted that it may be necessary to adjust the dose of a compound when it is administered in the form of a salt, such as, e.g., a laurate, the salt-forming moiety of which has an appreciable molecular weight. The general range of effective administration rates of the compounds is about 0.005 to about 100 mg/kg/day. A preferred rate range is from about 0.1 to about 30 mg/kg/day. Of course, it is often practical to administer the daily dose of a pharmaceutical compound in portions, at various hours of the day.

The route of administration of the compounds of this invention is not critical. The compounds are absorbed from the alimentary tract, and so it is usually preferred to administer them orally, for convenience. They may be administered, however, by any pharmaceutically acceptable route if desired in a given instance.

The compounds of this invention are usually administered as pharmaceutical compositions which are important and novel embodiments of the invention, because of the presence of the novel and valuable compounds. All of the usual types of pharmaceutical compositions may be used, however, including tablets, chewable tablets, capsules, solutions, parenteral solutions, suspensions, suppositories, and troches. Compositions are preferably formulated to contain a daily dose, or a convenient fraction of a daily dose, in a dosage unit which may be a single solid entity such as a tablet, or may be a convenient volume of a liquid or semi-solid. The activity of the compounds does not depend on the compositions in which they are administered or on the concentration of the compositions, and thus, the compositions are chosen and formulated solely for reasons of convenience and economy in use. Any of the compounds may be readily formulated as tablets, capsules and the like; it is obviously preferable to prepare solutions, such as those for injection, from water-soluble salts of the compounds.

In general all of the compositions are prepared according to methods usual in pharmaceutical chemistry. A group of typical formulae of compositions will be mentioned below, but the principles of such formulations are so well known that no detailed discussion will be provided.

| CAPSULES | |
|---|---|
| Formulation A | |
| Example 4 | 100 mg |
| microcrystalline cellulose | 300 mg |
| pregelatinized starch | 97 mg |
| silicone fluid | 3 mg |
| Formulation B | |
| Example 6 | 200 mg |
| pregelatinized starch | 100 mg |
| starch | 50 mg |
| silicone fluid | 2 mg |
| Formulation C | |
| Example 6 | 300 mg |
| pregelatinized starch | 200 mg |
| SOLUTIONS | |
| Formulation D | |
| Example 8, hydrochloride | 5 mg |
| deionized water | 5 ml |
| Formulation E | |
| Example 9, acetate | 25 mg |
| deionized water | 5 ml |
| TABLETS | |
| Formulation F | |
| Example 10 | 5 mg |
| microcrystalline cellulose | 240 mg |
| starch | 45 mg |
| stearic acid | 6 mg |
| magnesium stearate | 3 mg |
| colloidal silicon dioxide | 1 mg |
| Formulation G | |
| Example 12, benzoate | 150 mg |
| microcrystalline cellulose | 128 mg |
| lactose | 25 mg |
| pregelitanized starch | 10 mg |
| stearic acid | 8 mg |
| magnesium stearate | 3 mg |
| colloidal silicon dioxide | 2 mg |
| Formulation H | |
| Example 14 | 250 mg |
| calcium phosphate | 58 mg |
| lactose | 54 mg |
| microcrystalline cellulose | 31 mg |
| starch | 5 mg |
| stearic acid | 2 mg |
| magnesium stearate | 1 mg |

I claim:
1. A compound of the formula

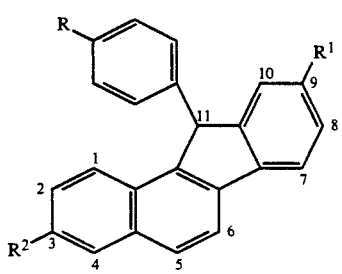

wherein R represents hydroxy or —O—$(CH_2)_n N(R^3)(R^4)$; $R^1$ represents hydrogen, hydroxy, $C_1$–$C_3$ alkoxy, halo, or —COR$^5$; R$^2$ represents hydrogen, hydroxy, C$_1$–C$_3$ alkoxy, or —COR$^5$; n represents 1–3; R$^3$ and R$^4$ independently represent C$_1$–C$_4$ n- or sec-alkyl; or R$^3$ and R$^4$ combine to represent butylene, pentylene or hexylene; R$^5$ represents C$_1$–C$_5$ alkyl, phenyl, or phenyl substituted with 1 or 2 groups chosen from halo, C$_1$–C$_3$ alkyl, hydroxy, and C$_1$–C$_3$ alkoxy;

and the physiologically acceptable acid addition salts thereof.

2. A compound of claim 1 wherein R is hydroxy.

3. A compound of claim 1 wherein R is —O—(CH$_2$)$_n$N(R$^3$)(R$^4$).

4. A compound of claim 1 wherein R$^1$ is hydrogen, hydroxy, or C$_1$–C$_3$ alkoxy.

5. A compound of claim 1 wherein R$^2$ is hydrogen, hydroxy, or C$_1$–C$_3$ alkoxy.

6. A compound of claim 4 wherein R$^2$ is hydrogen, hydroxy, or C$_1$–C$_3$ alkoxy.

7. A compound of claim 3 wherein R$^3$ and R$^4$ independently represent C$_1$–C$_3$ n-alkyl or combine to represent butylene, pentylene or hexylene.

8. A compound of claim 7 wherein n represents 2.

9. A compound of claim 8 wherein R$^1$ and R$^2$ independently represent hydrogen, hydroxy, or C$_1$–C$_3$ alkoxy.

10. The compound of claim 1 which is 3-methoxy-11-[4-(2-piperidin-1-ylethoxy)phenyl]-11H-benzo[a]fluorene or a physiologically acceptable salt thereof.

11. A pharmaceutical composition comprising a pharmaceutically acceptable carrier and a compound of claim 3.

12. A pharmaceutical composition comprising a pharmaceutically acceptable carrier and a compound of claim 6.

13. A pharmaceutical composition comprising a pharmaceutically acceptable carrier and a compound of claim 9.

14. A pharmaceutical composition comprising a pharmaceutically acceptable carrier and the compound of claim 10.

15. A method of inducing an estrogenic or anti-estrogenic effect in a subject in need thereof which comprises administering an effective amount of a compound of claim 3 to such subject.

16. A method of inducing an estrogenic or anti-estrogenic effect in a subject in need thereof which comprises administering an effective amount of a compound of claim 6 to such subject.

17. A method of inducing an estrogenic or anti-estrogenic effect in a subject in need thereof which comprises administering an effective amount of a compound of claim 9 to such subject.

18. A method of inducing an estrogenic or anti-estrogenic effect in a subject in need thereof which comprises administering an effective amount of the compound of claim 10 to such subject.

* * * * *